United States Patent
Weiss

(10) Patent No.: US 10,445,464 B2
(45) Date of Patent: *Oct. 15, 2019

(54) SYSTEM AND METHOD FOR DETECTING MEDICAL ANOMALIES USING A MOBILE COMMUNICATION DEVICE

(75) Inventor: Andrew Weiss, San Ramon, CA (US)

(73) Assignee: Location Labs, Inc., Emeryville, CA (US)

(*) Notice: Subject to any disclaimer, the term of this patent is extended or adjusted under 35 U.S.C. 154(b) by 947 days.

This patent is subject to a terminal disclaimer.

(21) Appl. No.: 13/399,887

(22) Filed: Feb. 17, 2012

(65) Prior Publication Data

US 2013/0218812 A1 Aug. 22, 2013

(51) Int. Cl.
| | | |
|---|---|---|
| G06F 19/00 | (2018.01) | |
| G06N 20/10 | (2019.01) | |
| G06N 7/00 | (2006.01) | |
| G06N 20/00 | (2019.01) | |
| G16H 50/20 | (2018.01) | |

(52) U.S. Cl.
CPC ......... *G06F 19/3418* (2013.01); *G06N 7/005* (2013.01); *G06N 20/00* (2019.01); *G06N 20/10* (2019.01); *G16H 50/20* (2018.01)

(58) Field of Classification Search
CPC .................................................. G16H 50/20
See application file for complete search history.

(56) References Cited

U.S. PATENT DOCUMENTS

| | | | |
|---|---|---|---|
| 5,285,586 A | 2/1994 | Goldston et al. | |
| 6,259,399 B1 | 7/2001 | Krasner | |
| 6,571,193 B1* | 5/2003 | Unuma et al. | 702/141 |
| 6,819,258 B1 | 11/2004 | Brown | |
| 6,961,562 B2 | 11/2005 | Ross | |
| 7,042,338 B1 | 5/2006 | Weber | |
| 7,046,147 B2 | 5/2006 | Stigall | |
| 9,071,939 B2 | 6/2015 | Hategan et al. | |
| 9,147,336 B2 | 9/2015 | Schultz et al. | |
| 2002/0120187 A1* | 8/2002 | Eiffert et al. | 600/407 |
| 2004/0030531 A1* | 2/2004 | Miller et al. | 702/182 |
| 2006/0136393 A1* | 6/2006 | Abbott | G06F 17/30867 |
| 2007/0136102 A1* | 6/2007 | Rodgers | 705/3 |

(Continued)

FOREIGN PATENT DOCUMENTS

DE EP 2264988 12/2010

OTHER PUBLICATIONS

Hendrich, Ann "Predicting Patient Falls" AJN Nov. 2007 vol. 107, No. 11 [Online] Downloaded Oct. 16, 2014 http://www.lmsresourceinfo.com/media/Falls%20-%20Predicting%20Patient%20Falls.pdf.*

(Continued)

*Primary Examiner* — Ben M Rifkin

(74) *Attorney, Agent, or Firm* — Dovas Law, P.C.

(57) ABSTRACT

A computer-implemented method is provided including receiving sensor data from a mobile device corresponding to a first user. A user state of the first user is predicted based on the sensor data. A request is transmitted to the first user to confirm the predicted user state, and a notification is transmitted regarding the predicted user state to a second user responsive to the first user's confirmation of the predicted user state or the first user's failure to respond to the request. A computing system for monitoring and reporting activity of a mobile device is also provided.

42 Claims, 3 Drawing Sheets

(56) References Cited

U.S. PATENT DOCUMENTS

| | | | |
|---|---|---|---|
| 2008/0139899 A1* | 6/2008 | Student | A61B 5/1112 600/301 |
| 2010/0007503 A1 | 1/2010 | Carrington | |
| 2010/0049095 A1* | 2/2010 | Bunn | A61B 5/1038 600/595 |
| 2010/0142715 A1 | 6/2010 | Goldstein et al. | |
| 2010/0267361 A1 | 10/2010 | Sullivan | |
| 2011/0205051 A1 | 8/2011 | Katingari et al. | |
| 2011/0207408 A1 | 8/2011 | Lefebvre | |
| 2011/0294457 A1 | 12/2011 | Braznell | |
| 2012/0196538 A1 | 8/2012 | Mateu | |
| 2012/0316456 A1 | 12/2012 | Rahman et al. | |
| 2013/0021788 A1 | 1/2013 | Mayes | |
| 2013/0150117 A1 | 6/2013 | Rodriguez et al. | |
| 2013/0214925 A1 | 8/2013 | Weiss | |
| 2013/0297547 A1 | 11/2013 | Ding et al. | |
| 2014/0024399 A1 | 1/2014 | Shimo et al. | |
| 2014/0099972 A1 | 4/2014 | Weiss | |
| 2015/0249904 A1 | 9/2015 | Weiss et al. | |
| 2016/0100293 A1 | 4/2016 | Weiss | |

OTHER PUBLICATIONS

Glick, henry "Introduction to Markov MOdels" Jul. 2007 [Online] Downloaded Oct. 16, 2014 http://www.uphs.upenn.edu/dgimhsr/acadcrs/korea07/08.markovmodels.pdf.*

Doukas, Charalampos et al "Patient Fall Detection using Support Vector Machines" 2007 international Federation for Information Processing, vol. 247 [Online] Downloaded Oct. 16, 2014 http://download.springercom/static/pdf/534/chp%253A10.1007%252F978-0-387-74161-1_16.pdf?auth66=1413472105_a535aa368cd19e5f11410aa309aec530&ext=.pdf.*

Rifkin, Ryan and Aldebaro Klautau "In Defense of One-Vs-All Classification" The Journal of Machine Learning Research 2004 [Online] Downloaded Oct. 16, 2014.*

Kim, Kyu-jin et al "Dementia Wandering Detection and Activity Recognition Algorithm Using Tri-axial Accelerometer Sensors" IEEE 2009 [Online] Downloaded Feb. 1, 2016 http://ieeexplore.ieee.org/xpls/abs_all.jsp?arnumber=5405672&tag=1.*

C. Thompson, J. White, B. Dougherty, A. Albright and D.C. Smith, "Using Smartphones to Detect Car Accidents and Provide Situational Awareness to Emergency Responders"Third International Conference-Mobileware, Jun. 2010.

* cited by examiner

SYSTEM AND METHOD FOR DETECTING MEDICAL ANOMALIES USING A MOBILE COMMUNICATION DEVICE

BACKGROUND

There is a segment of the population which would benefit from active behavioral monitoring and behavioral assessment to detect medical anomalies. Active behavioral monitoring and assessment may be particularly beneficial to the elderly, the disabled, and those recovering from surgery or recent trauma, especially when such persons are not located in a facility that provides appropriate patient supervision. Persons who are cognitively disabled for example may be more likely to become lost or disoriented. Persons who are physically disabled for example may be more likely to fall and become unconscious. Certain persons' medical history may distinguish them to be more likely to have a seizure. Timely detection of a medical anomaly such as disorientation, seizure, or physical injury is often critical to prevent injury, aggravation of an existing condition, or fatality.

SUMMARY

The invention provides a computer-implemented method including receiving sensor data from a mobile device corresponding to a first user. A user state of the first user is predicted based on the sensor data. A request is transmitted to the first user to confirm the predicted user state, and a notification is transmitted regarding the predicted user state to a second user responsive to the first user's confirmation of the predicted user state or the first user's failure to respond to the request.

A computing system including at least one memory comprising instructions operable to enable the computing system to perform a procedure for monitoring and reporting activity of a mobile device corresponding to a first user, the procedure including receiving sensor data from a mobile device corresponding to a first user. A user state of the first user is predicted based on the sensor data. A request is transmitted to the first user to confirm the predicted user state, and a notification is transmitted regarding the predicted user state to a second user responsive to the first user's confirmation of the predicted user state or the first user's failure to respond to the request.

Non-transitory computer-readable media tangibly embodying a program of instructions executable by a processor to implement a method for controlling activity of a mobile device corresponding to a first user, the method including receiving sensor data from a mobile device corresponding to a first user. A user state of the first user is predicted based on the sensor data. A request is transmitted to the first user to confirm the predicted user state, and a notification is transmitted regarding the predicted user state to a second user responsive to the first user's confirmation of the predicted user state or the first user's failure to respond to the request.

BRIEF DESCRIPTION OF THE DRAWING(S)

The foregoing Summary as well as the following detailed description will be readily understood in conjunction with the appended drawings which illustrate embodiments of the invention. In the drawings.

DETAILED DESCRIPTION OF ILLUSTRATIVE EMBODIMENT(S)

Figure 1:
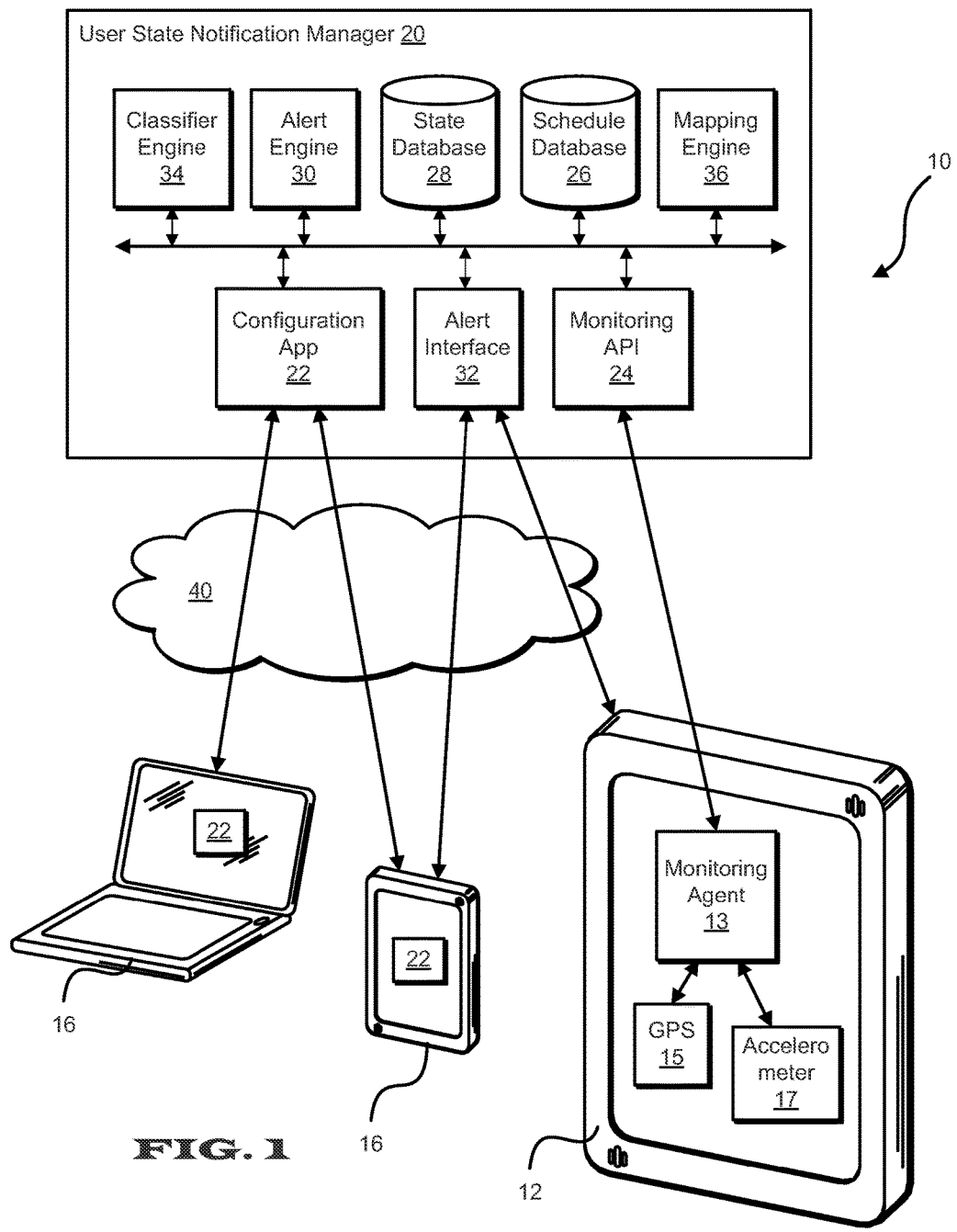
FIG. 1 shows a system for providing a user state notification according to the invention.

Embodiments of the invention are described below with reference to the drawing figures where like numerals represent like elements throughout.

Referring to FIG. 1, a system 10 is provided including a user state notification manager 20 ("notification manager 20") used for providing notification regarding a particular user's state to another user. The user's state preferably corresponds to the user's physical condition, for example whether the user is predicted to have fallen or to have become unconscious, whether the user is predicted to be disoriented or having a seizure or experiencing other medical anomaly. The state notification manager 20 enables a configuration application 22, a monitoring application program interface ("API") 24, a schedule database 26, a state database 28, an alert engine 30, an alert interface 32, a classifier engine 34 and a mapping engine 36. The notification manager 20 can be implemented on one or more network accessible computing systems in communication via a network 40 with a mobile communication device 12 which corresponds to a monitored user and is monitored via a monitoring agent 13. Alternatively, the notification manager 20 or one or more components thereof can be executed on the monitored mobile communication device 12 or other system. The configuration application 22 includes a web application or other application enabled by the notification manager 20 and accessible to the client device 16 via a network and/or executed by the client device 16.

Software and/or hardware residing on a monitored mobile communication device 12 enables the monitoring agent 13 to provide an indication of a medical anomaly to the notification manager 20 via the monitoring API 24, or alternatively, to provide the notification manager 20 with data for determining a medical anomaly. The mobile device 12 can include for example a smartphone or other cellular enabled mobile device preferably configured to operate on a wireless telecommunication network. In addition to components enabling processing and wireless communication, the mobile device 12 includes a global positioning system (GPS) receiver 15 and an accelerometer 17 from which the monitoring agent 13 gathers data used for predicting a user's state. A monitored user carries the mobile device 12 on their person with the monitoring agent 13 active.

Figure 2:
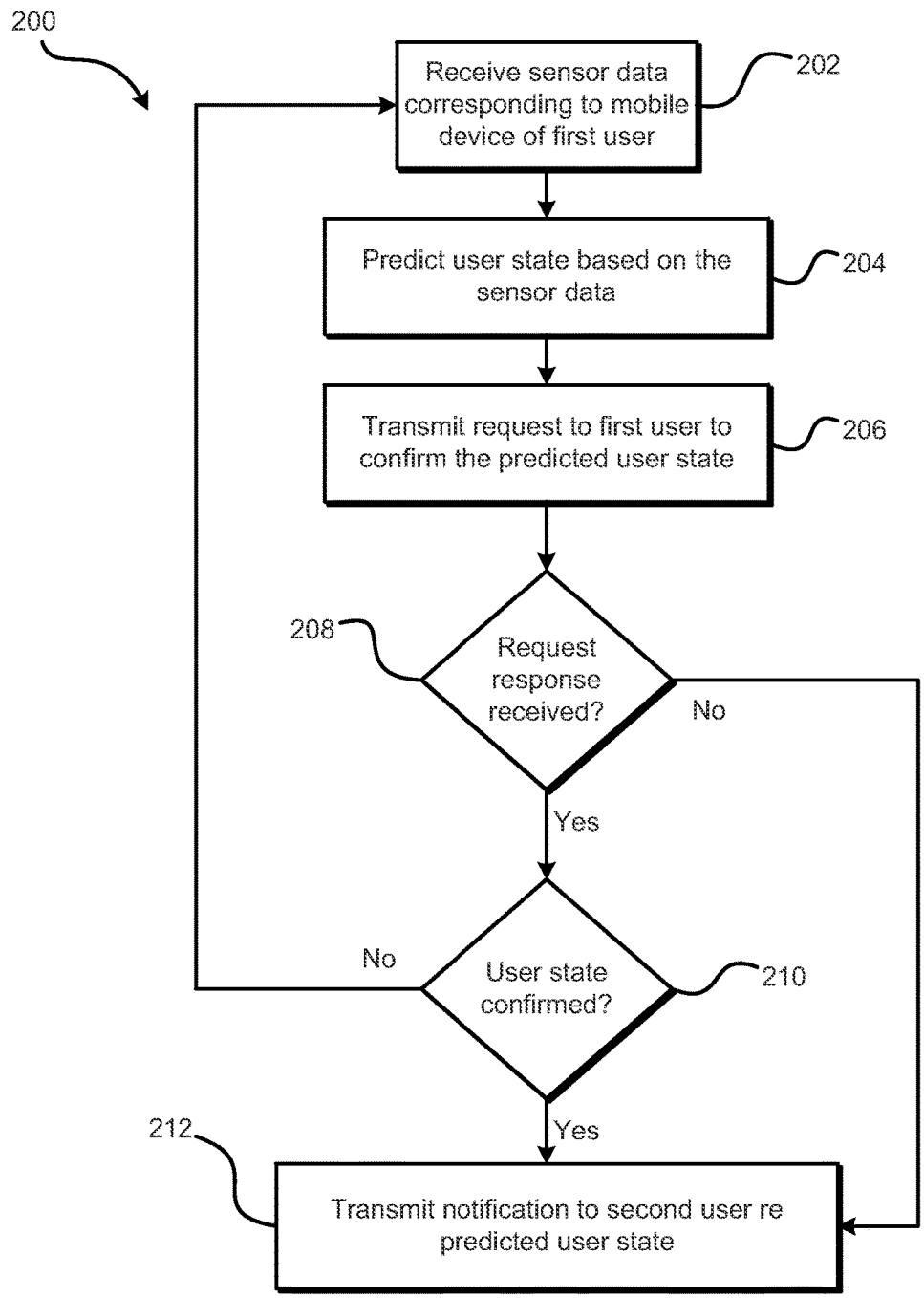
FIG. 2 is a diagram showing a method for providing a user state according to the invention.

Referring to FIG. 2, a method 200 for providing notification of a user state is shown. The method 200 is described with reference to the components shown in the system 10 of FIG. 1, including the notification manager 20 and monitoring agent 13, which are preferably configured for performing the method 200. The method 200 may alternatively be performed via other suitable systems. The method 200 includes receiving sensor data from a mobile device, for example the mobile device 12, the sensor data corresponding to a first user (step 202), for example a monitored user. A user state of the first user is predicted based on the sensor data (step 204). The predicted user state preferably corresponds to a medical anomaly, for example a prediction that the user has fallen ("fall state"), has become unconscious ("unconscious state"), has become disoriented or is wandering ("wandering state"), or has experienced a seizure ("seizure state"). A request is transmitted to the first user, for example via the mobile device 12, to confirm the predicted user state (step 206). If a response to the request is not received (step 208) or a response is received confirming the predicted user state (step 210), a notification regarding the predicted user state is transmitted to a second user (step 212), a monitoring user, for example a notification generated by the alert engine 30 transmitted via the alert interface 32. Alternatively, if the first user responds with an indication that the predicted user state is invalid (step 210), the process returns to step 202 and a notification is not transmitted to the second user.

The sensor data preferably includes device acceleration data from an accelerometer 17 on the mobile device 12. The sensor data can further include position, time and velocity data from the GPS receiver 15. Sensor data can be resolved to predict the user state by executing a classifier on the mobile device 12, for example via the monitoring agent 13, or by executing the classifier on a remote system in communication with the mobile device 12 through a network, for example via the notification manager 20. In addition to sensor data, a collection of predetermined conditions, provided for example by a monitoring user via a device 16, can be input to the classifier for determining the user state. The classifier includes an algorithm for identifying the states to which new observations belong, where the identity of the states is unknown. The classifier is trained prior to implementation based on received training data including observations corresponding to known states and can be continually retrained based on new data to enable a learning process.

The request to confirm the predicted user state can be transmitted from the notification manager 20 to a monitored user via the monitoring agent 13 on the monitored user's mobile device 12. The notification manager 20 is configured to receive via the monitoring agent 13 a confirmation from the monitored user that the prediction of the user state is valid or an indication that the prediction of the user state is invalid. For example, a one touch user interface can be enabled by the monitoring agent 13 to allow the monitored user to confirm or invalidate the predicted user state. A test questionnaire can be provided to the monitored user to permit confirmation or invalidation of one or more determined user states. Alternatively, the request to the monitored user to confirm the predicted user state can be performed by initiating a telephone call to the monitored user's mobile device 12, for example via the alert interface 32, wherein the user response can be received as a voice or tone signal. Alternatively, transmitting the request or receiving a response from the monitored user can be performed by any suitable synchronous or asynchronous communication process. Collected sensor data is selectively applied by the classifier engine 34 to the classifier from which the state was determined with the indication that the prediction of the user state is valid or invalid to retrain the classifier. A request can further be provided to a monitoring user, for example via the client device 16, to confirm the predicted user state, which responsive data can be further used in a classifier retraining process.

The classifier preferably includes a plurality of components, wherein each component is configured to resolve a particular collection of inputs to predict the user state. A component for predicting a user has fallen down ("fall state") is configured to resolve sensor data including device acceleration data, for example from accelerometer 17, and device position data with associated time data, for example from the GPS receiver 15. The classifier component for detecting a fall state for the user can be defined using a predetermined decision tree acting from accelerometer inputs, optionally conditioned by a Markov model for a potential improvement in accuracy. Velocity data, derived for example from the GPS receiver 15 ("GPS velocity data"), can be used to confirm a fall state, for example, by confirming that the user has no apparent velocity or small apparent velocity, the latter accounting for any error in velocity determination.

A classifier component for predicting a user is wandering or disoriented ("wandering state") is configured to resolve sensor data including device acceleration data, device position data, and optionally, device velocity data (e.g. GPS velocity data). The wandering state can be determined for example by determining a distance traveled by a first user based on the position data over a particular predetermined time period, determining a distance between a first point at a start of the predetermined time period and a second point at an end of the predetermined time period, and predicting the wandering state based on the distance traveled and the distance between the first point and the second point. For example, the detection of wandering may take as input the ratio of a series of GPS readings that reflect the distance covered by the monitored user over some period of time, divided by the distance between the endpoints of that path; the ratio can be an input into a decision tree that is a classifier component for this wandering behavior.

Alternatively, a wandering state can be determined by determining a "walking state" that lacks purposeful intent, wherein purposeful intent is deemed present responsive to the monitored user stopping at a friend's home, stopping at a venue, or stopping at another significant location. Lack of purposeful intent follows a general demonstration of a lack of stopping during a prolonged period of walking or other traveling manner. Significant locations can be designated for example by the notification manager 20 or via inputs by the monitoring user. A monitored user's failure to stop for a predetermined period of time at the designated location in his or her path of travel, as determined from the position data, can result in a prediction of the wandering state. Conversely, visits to friends, venues, or extended stops at particular locations demonstrate an intent to visit, as opposed to an aimless walk, providing evidence of purposeful intent opposing a prediction of a wandering state. GPS velocity data and accelerometer data can be used to confirm that the monitored user is walking or traveling in another manner. The locations of homes of friends of the monitored user, and venues in an area frequented by the monitored user, can be included as part of the state database 28. Known or suspected prior ingestion of medication known to possibly cause a disoriented state can also be included as a condition for deriving the classification of wandering behavior.

A classifier component for predicting a user is unconscious ("unconscious state") is configured to resolve sensor data including device acceleration data, device position data, and device velocity data. The position data can include an indication of the distance traveled, if any distance is traveled during a predetermined time period. For example, the classifier component can include a decision tree acting from accelerometer inputs with secondary processing by a Markov model, which is used in conjunction with a support vector machine which takes as input distance covered, derived from GPS readings, to confirm lack of motion. A predetermined condition that indicates that the user may be affected by medication ingested at some threshold prior period of time, in a way that increases the probability of an unconscious state, can also be an input to this support vector machine.

As an alternative to implementing a single classifier with multiple components for predicting multiple user states, a plurality of classifiers can be applied to the sensor data to predict a user state, wherein each of the plurality of classifiers corresponds to one or more user states, for example a fall state classifier, a wandering state classifier and an unconscious state classifier.

A classifier can include a decision tree or other static or dynamic classifier and can be conditioned by a Markov model. The classifier can be trained based on received training data including sensed data from a particular device and an indication of one or more known states corresponding to the sensed data. For example, sensor data from a mobile device carried by or attached to a test user known to have experienced a fall state, an unconscious state, a wandering state, or a seizure state when the test data was generated can be used to train the classifier. Alternatively, sensor data from a mobile device carried by or attached to a test user who physically simulates a fall state, an unconscious state, a wandering state, or a seizure state when the test data is generated can be used to train the classifier. Training sensor data is received via the configuration application 22 of the notification manager from a test device, training is performed via the classifier engine 34, and trained classifiers are stored in the state database 28. To predict a user state of a monitored user, trained classifiers are applied to sensor data from a monitored device 12. A classifier can be executed locally on the device 12, for example via the monitoring agent 13, or on a remote system which receives the sensor data via a network, for example via the classifier engine 34 of the notification manager 20 implemented on a network-accessible system.

The confirmation/refutation of predicted user states, from either the monitored user through the device 12, or the monitoring user through the device 16, can be used as training data to re-train classifiers used to predict the user states. For example, if the classifier (or classifiers) predicts that the user is unconscious ("unconscious state"), and a corresponding confirmation request is sent to the monitored user, which the monitored user refutes, then the classifier or classifiers used to make the unconscious state prediction can be incrementally retrained based on the refutation. The classifier or classifiers in the classifier engine 34 are updated accordingly.

The notification manager 20 is further configured to receive an indication of a geographic area, for example from the monitoring user via the configuration application 22, and to determine if the monitored device has entered or exited the geographic area. The user state of the monitored user is predicted based on the indication of the geographic area if the monitored device has entered, or alternatively, exited the geographic area. The indication of the geographic area includes a designation that the first user is predicted to be active or passive in the geographic area, wherein a classifier used for predicting the user state is specific to the geographic area corresponding to an active designation, and a classifier used for predicting the user state is specific to the geographic area corresponding to a passive designation. The indication that the monitored user has entered, or alternatively exited, the geographic area along with the geographic area's designation is provided as an input to a classifier. For example, if the geographic area corresponds to the bedroom of a monitored user, and the designation indicates the user is likely to be passive therein, that is, likely to be asleep when in the bedroom, the classifier used to predict an "unconscious state" or "wandering state" is one conditioned for passive behavior, when, based on position data, the user is determined to be in the bedroom. Conversely, if the geographic area corresponds to a particular undeveloped wilderness area, and the designation indicates the user is likely to be active, that is, likely to be disoriented when in the particular undeveloped wilderness area, the classifier to used to predict an "unconscious state" or "wandering state" is one conditioned for active behavior, when, based on position data, the user is determined to be in the particular undeveloped wilderness area. A first classifier can be applied when the geographic area where the monitored user is located corresponds to an passive designation and a second classifier can be applied when the geographic area where the monitored user is located corresponds to a active designation, wherein the second classifier is trained to be more likely to predict the user state than the first classifier given the same input data. In one example implementation, a threshold for predicting the user state can be relatively higher if the geographic area corresponds to an active designation, and a threshold for predicting the user state can be relatively lower if the geographic area corresponds to a passive designation.

In another implementation, predicting the user state or transmitting the notification to a monitoring user of a predicted user state are performed responsive to determining the mobile device has entered, or alternatively, exited the geographic area, wherein the monitored user's entrance to or exit from the geographic area operates as a trigger to initiate monitoring of a user, allowing the classifier to generate a user state prediction and allowing the monitoring user to be notified of the predicted user state. For example, a user who is located in a geographic area corresponding to a hospital or care facility may not require monitoring until such time as the user leaves the hospital or care facility.

In another implementation, the notification manager 20 is configured to receive an indication of a geographic area from a user with an indication of a predetermined time period. The mobile device is determined to have entered or exited the geographic area, for example determined via the mapping engine 36. Entering, or alternatively, exiting the geographic area during the predetermined time period triggers monitoring of a monitored user, wherein predicting the user state and transmitting a notification regarding the user state to a monitoring user is performed responsive to determining the mobile device has entered or exited the geographic area during the predetermined time period. For example, a monitored user's presence outdoors at a particular public park between 10 pm and 6 am triggers monitoring by the monitoring agent 13, whereas a monitored user's presence at the public park between the hours of 6 am and 10 pm does not trigger monitoring and predicting a user state.

The notification manager 20 is further configured to determine a venue corresponding to a particular geographic area using mapping data including business directory information, compiled for example via the mapping engine 36. In addition to sensor data, venue data is input to the classifier and the user state is based further on the determined venue responsive to the mobile device entering or exiting the geographic area. The geographic area corresponding to the determined venue can correspond to a classifier trained for predicting the user state corresponding to that venue. For example, if a monitored user is determined to enter a geographic area determined to correspond to a bowling alley venue or a fitness center venue, the classifier used to predict a "fall state" is a classifier that has been trained to recognize a fall state while bowling, or engaged in otherwise active behavior which approximates that of bowling behavior, since it is likely that normal activity in such environments may produce acceleration data mimicking a fall state. More generally, different classifiers can correspond to different venues, wherein given the same input data, a particular classifier corresponding to a particular venue is configured to be more or less likely to predict a particular user state than a default classifier not corresponding to a venue or a classifier corresponding to another venue. Thus, for example, the accelerometer output corresponding to a fall while bowling may be different from output generated by walking. Employing a different classifier for each user state can improve the probability for detecting a targeted behavior. In one example implementation, the geographic area corresponding to the determined venue can correspond to a higher or lower threshold for predicting the user state than a geographic area not corresponding to the venue.

The notification manager 20 is further configured to receive predetermined condition data, for example from a monitoring user, and predict the user state of a monitored user using the classifier engine 34 based on the sensor data and the predetermined condition data. The predetermined condition can correspond to a predetermined schedule stored in the schedule database 26, wherein the user state is predicted based on a classifier determined by the predetermined schedule. For example, the predetermined condition data can include an indication of when the first user is scheduled to be medicated. A first classifier for predicting the user state corresponds to a period when the monitored user is not scheduled to be medicated. A second classifier for predicting the user state corresponds to a period when the monitored user is scheduled to be medicated, or more specifically, a predetermined period of time after medication is scheduled to be administered. The user state of the monitored user is predicted based on the first classifier during the period when the monitored user is not scheduled to be medicated, and the user state of the monitored user is predicted based on the second classifier when the monitored user is scheduled to be medicated. A plurality of different classifiers can be trained for a plurality of different medications, wherein different classifiers correspond to different medications, and user state determinations are influenced by the particular medication scheduled to be administered.

Alternatively, a designation that a user is not scheduled to be medicated or is scheduled to be medicated with a particular medication can be provided as an input to a single classifier for determining the user state. The single classifier can be trained with data that includes a factor describing whether the user is in a medicated state, has been recently medicated, is in a state such that the prime side effects of the medication may be evident, or the user is in a post-medicated state where the likelihood of the manifestation of a side effect is relatively small. For example, the classifier can be trained such that it is more likely to determine a particular user state (e.g. a fall state, an unconscious state, a wandering state, or a seizure state) when the user is scheduled to be medicated. In training the classifier, the notification manager 20 via the classifier engine 34 can determine one or more effects or side-effects of the medication which is scheduled to be administered. For example, a parameter of a classifier for determining a fall state or unconscious state can correspond to a predetermined time period after a drowsiness-causing medication is scheduled to be administered. As an additional benefit, the notification manager 20 via the alert interface 32 can provide a reminder notification to the monitored user when the scheduled time for the monitored user to take medication arrives.

In one example implementation, a first threshold for predicting the user state corresponds to a period when the monitored user is not scheduled to be medicated. A second threshold for predicting the user state corresponds to a period when the monitored user is scheduled to be medicated, or more specifically, a predetermined period of time after medication is scheduled to be administered. The user state of the monitored user is predicted based on the first threshold during the period when the monitored user is not scheduled to be medicated, and the user state of the monitored user is predicted based on the second threshold during the period when the monitored user is scheduled to be medicated. The second threshold can correspond for example to a lower threshold such that for given data input (e.g. position data, acceleration data), it is more likely to predict a particular user state (e.g. a fall state, an unconscious state, a wandering state, or a seizure state) when the user is scheduled to be medicated.

The predetermined condition data can alternatively include an indication of one or more disabilities or medical conditions associated with the monitored user. For example, a parameter of a classifier for determining a fall state or unconscious state can correspond to a monitored user indicated as having a physical disability, a parameter of a classifier for determining a seizure state can correspond to a monitored user indicated as having a history of seizures, and a parameter of a classifier for determining a wandering state can correspond to a monitored user indicated as diagnosed with a cognitive disability. The seizure state can be predicted for example based on acceleration data from an accelerometer and the indication of one or more disabilities or medical conditions associated with the monitored user. For example, as compared to a monitored user without disability, a lower threshold for determining a fall state or unconscious state can correspond to a monitored user indicated as having a physical disability, a lower threshold for determining a seizure state can correspond to a monitored user indicated as having a history of seizures, and a lower threshold for determining a wandering state can correspond to a monitored user indicated as diagnosed with a cognitive disability.

The predetermined condition data can alternatively include an indication that a monitored user is scheduled to be performing a particular physical activity. A first classifier for predicting the user state corresponds to a period when the monitored user is not scheduled to be performing the particular physical activity. A second classifier for predicting the user state corresponds to a period when the monitored user is scheduled to be performing the particular physical activity. The user state of the monitored user is predicted based on the first classifier during the period when the monitored user is not scheduled to be performing the particular physical activity, and the user state of the monitored user is predicted based on the second classifier when the user is scheduled to be performing the particular physical activity. Different classifiers for determining a fall state, a seizure state or an unconscious state can correspond to a time period where a monitored user is scheduled to be participating in a physical activity such as bowling, or jogging to decrease the risk of a false determination of a fall state, a seizure state or an unconscious state.

For example, a first classifier (e.g. a default classifier) can be used for predicting the user state when the monitored user is not scheduled to be performing a particular physical activity, and a second classifier can be used when the monitored user is scheduled to be performing the particular physical activity, which second classifier is trained for predicting the user state when the monitored user is engaged in the particular physical activity. A plurality of different classifiers respectively weighted towards particular physical activities can be trained for predicting user state when the monitored user is scheduled to be performing the particular physical activities. For example, a particular classifier different from a default classifier(s) can be used for determining a fall state, a seizure state or an unconscious state when a monitored user is scheduled or determined to be bowling, and another classifier can be used for determining such state when the user is scheduled or determined to be jogging. Alternatively, a designation that a user is scheduled or determined to be performing a particular physical activity can be provided as an input to a single classifier (e.g. the default classifier). Alternatively, monitoring of a user can be discontinued entirely during such time when the monitored user is scheduled or determined to be participating in a particular physical activity.

In an example implementation, a first threshold for predicting the user state corresponds to a period when the monitored user is not scheduled to be performing the particular physical activity, a second threshold for predicting the user state corresponds to a period when the monitored user is scheduled to be performing the particular physical activity, and the user state of the monitored user is predicted based on the first threshold during the period when the monitored user is not scheduled to be performing the particular physical activity, and the user state of the monitored user is predicted based on the second threshold when the user is scheduled to be performing the particular physical activity. The second threshold can correspond for example to a higher threshold such that for given data input (e.g. position data, acceleration data), it is less likely to predict a particular user state (e.g. a fall state, an unconscious state, a wandering state, or a seizure state) when the user is scheduled to be performing the particular physical activity.

Figure 3:
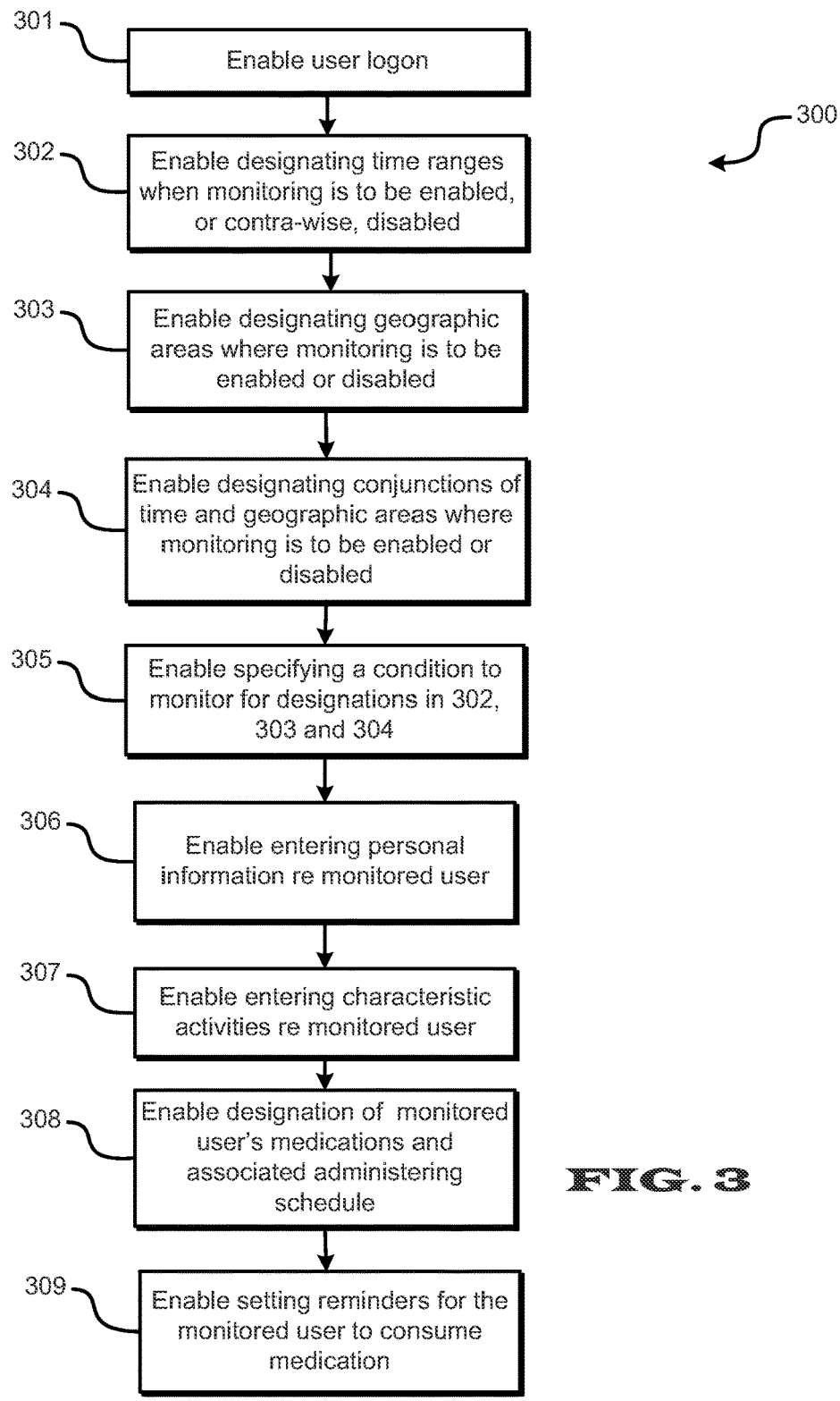
FIG. 3 is a diagram showing a user configuration process for enabling monitoring of a mobile communication device according to the invention.

Referring to FIG. 3, a user configuration process is shown for enabling monitoring of a mobile communication device 12 via the notification manager 20. In a step 301, the notification manager enables a monitoring user to logon from a client device 16 via the configuration application 22. The monitoring user is enabled to designate time ranges when monitoring is to be enabled, or contra-wise, disabled (step 302). The monitoring user is enabled to designate geographic areas where monitoring is to be enabled, or contra-wise, disabled (step 303). The monitoring user is enabled to designate conjunctions of time and geographic areas where monitoring is to be enabled or disabled (step 304). The monitoring user is also enabled to specify a condition to monitor for each of the entries defined in step 302, 303, and 304 (step 305), for example monitor for lack of motion or an unconscious state if a current position of a monitored device 12 corresponds to a tennis court. Alternatively, the monitoring user can specify conditions to bypass for such entries, for example do not monitor for inactivity or an unconscious state in the monitored user's bedroom between 11 pm and 8 am. The monitoring user is enabled to enter personal information about the monitored user, such as their birth date, name, ambulatory state (e.g. walking, using crutches, wheelchair, bedridden), or other identifying information or indication of disability (step 306). The monitoring user is enabled to enter information about activities in which the monitored user characteristically engages, such as walks in the park (indicating the location of the park), bowling, location of doctors' offices frequented by the monitored user, or indications of other activities commonly performed by the monitored user (step 307). The monitoring user is further enabled to input medications that the monitored user is currently taking, and the schedule the monitored user is to follow in taking this medication (step 308), which input can be maintained in the schedule database 26. The notification manager 20 via the classifier engine 34 is configured to determine effects and side-effects that may result from specified medications. The monitoring user is further enabled to set the system to notify the monitored user when the monitored user should be taking certain medication (step 309).

The mapping engine 36 may also deduce locations, and times that the monitored user frequents the locations, and suggest these to the monitoring user for registry (steps 302 and 303). For example, the mapping engine 36 may determine that the monitored user remains at 123 Main St. on Monday, Wednesday, and Friday between 4:00 PM and 5:00 PM, and suggest to the monitoring user via the configuration application 22 that this may be a location and time period for which explicit activity monitoring can be applied. The monitoring user may for example designate this location as corresponding to the home of a friend of the monitored user that the monitored user is visiting during the particular time period on the particular days.

An example implementation of the system 10 and associated method 200 follows. The system 10 via the monitoring agent 13 monitors the monitored user based on data from the mobile device GPS receiver 15 and accelerometer 17, passing the collected data through one or more classifiers to decide whether a medical anomaly has been detected. If the monitored user has recently (within a predetermined time period) taken medication with possible medical anomaly causation, this information is included as an input to the classifier. Other state data such as location, time of day, and projected activity, if available, are included as inputs to the classifier or classifiers. When a user state is determined, for example via the classifier engine 34, the alert interface 32 or other system component contacts the monitored user, for example via the mobile device 12, and requests that the monitored user verify their current state. For example, if the monitored user is determined to be potentially unconscious ("unconscious state"), a phone call initiated via the alert interface 32 can ask that the user press the number "7" on their phone to validate that they are not unconscious. If the user is determined to have possibly fallen ("fall state"), the notification manager 20 can call the monitored user via the alert interface 32, and request that the monitored user press the number "7" to indicate that they are fine, or the number "3" to indicate that they have fallen, or say, "I have fallen." The alert interface 32 is enabled to recognize a collection of phrases that may be spoken by the user that indicate the state of the user. If the user is detected to be wandering erratically ("wandering state"), the user can be provided a series of questions to ensure clarity of thought, such as "enter the day of the week, with Sunday being 1", "enter the sum of 5+8", "enter year of birth", or other suitable test questionnaire. If the monitored user is able to signal to the notification manager 20 that the monitored user is fine (e.g. the predicted user state is invalid), the system saves the detected location and accelerometer readings that lead to the erroneously detected anomaly for further analysis or to retrain the classifier. If the monitored user is not able to signal that the monitored user is fine after a predetermined period of time, for example 1 minute, or the monitored user signals that he or she is experiencing an anomalous medical condition (e.g. the predicted user state is valid), the notification manager 20 via the alert interface 32 contacts the monitoring user, for example via a client device 16, and provides the monitoring user the current location of the monitored user. The notification manager 20 is configured to give the monitoring user a continuous update as to the location of the user. The notification manager 20 also provides an update to the monitoring user as to the detected anomalous medical condition associated with the user state.

The classifier engine 34 is configured to determine one or more user states, classifiers for which can be stored for example in the state database 28. In determining the "fall state" the accelerometer 17 on the mobile device 12 is a source of data to detect the rapid vertical acceleration indicative of a falling condition. Further accelerometer readings signaling a post fall state in conjunction with locations and other device position data derived from the mobile device GPS 15 are used to confirm the fall state. It can be useful to apply other classifiers (not connected with the classifier to determine the fall state) to this data to determine the possibility that the user may be engaged in a particular activity and has not fallen. For example, a driving classifier can be applied to the same accelerometer and location data to determine the possibility that the monitored user may be driving. Other classifiers can be applied to the data to determine if the monitored user is for example playing tennis, bowling, jogging or participating in another activity corresponding to a particular unique user state. If it is determined that another user state corresponds to the data, the threshold for determining a fall state can be increased or a determination of a fall state can be precluded. For example, the weighting of the classifier for determining the fall state can be modified responsive to determining the other user state. The mapping engine 36 can attempt to derive the venue of the location in which the fall may have occurred. The determination of the venue can be included as an input to the classifier. For example, if it is determined that the venue is a bowling alley, and the user has a personal preference for bowling, this will act to decrease the probability that a fall has been detected, that is increase the threshold for determining the fall state for the corresponding geographic area.

The classifier engine 34 is further configured to determine the "unconscious state". The accelerometer 17 on the mobile device 12 is a source of data to detect relative inactivity that is indicative of the unconscious state. This data can be combined with data about the monitored user, such as geographic areas or venues where the monitoring user has indicated that the monitored user is likely to be in an active state, geographic areas where the monitoring user has indicated that the monitored user is likely to be in a passive state, or times when the monitoring user has designated that the monitored user is likely to be active or passive. Condition data, for example indicating that the user recently took medication which may induce an unconscious state, can also be included as input to the classifier.

The classifier engine 34 is further configured to determine the "wandering state". Erratic wandering is a behavior that can be expressed by users suffering from some form of dementia or other cognitive disability. A classifier which combines location, accelerometer readings, and GPS-determined velocity can be used to determine erratic wandering. Periodic location sampling can be used to determine if there is a consistent intention of direction, as opposed to what is classified as a random walk. Accelerometer reading can be used to determine if the gait of walking is undirected, staggering, or characterized by frequent stops and starts. GPS-determined velocity can be used to determine if the user is in a moving vehicle, such as a bus, train or car. Location outside of a geographic area can be used to determine that user is outside of a predetermined "safe zone". These data sources can be input to the classifier to make the determination as to the wandering state.

The classifier engine 34 is further configured to determine the "seizure state". Seizures are characterized by rhythmic muscle contractions. A classifier can take accelerometer data and GPS determined location data to determine the onset and duration of a seizure. Accelerometer data which records the rhythmic muscle contractions characteristic of muscle spasms can be fed to the classifier. Seizures are characterized by immobilized user behavior. Location data can be used to detect that the monitored user is not moving.

Some medications may cause seizures. Pregnancy can be a factor in seizures. Pre-existing conditions such as epilepsy, brain tumors, low blood sugar, parasitic infections, or other disability may be a factor in the likelihood of a seizure. These factors, provided by the monitoring user or other source, can be included as inputs to the classifier for determining the likelihood that the user is having a seizure. If a seizure is detected, the time at which it is detected and the duration of the seizure can be recorded by notification manager 20 and reported to the monitoring user.

While embodiments of the invention have been described in detail above, the invention is not limited to the specific embodiments described above, which should be considered as merely exemplary. Further modifications and extensions of the invention may be developed, and all such modifications are deemed to be within the scope of the invention as defined by the appended claims.

What is claimed is:

1. A computer-implemented method comprising:
    receiving training data comprising sensed data and an indication of at least one known state corresponding to the sensed data;
    training at least one classifier using the training data;
    receiving sensor data comprising at least accelerometer acceleration data from a mobile device corresponding to a first user;
    determining a business venue corresponding to a geographic area based on mapping data comprising business directory information;
    determining the mobile device has entered the geographic area;
    receiving predetermined condition data comprising an indication of when the first user is scheduled to be medicated with a medication;
    determining at least one effect or side-effect of the medication;
    determining a period when the first user is scheduled to be medicated based on the indication of when the first user is scheduled to be medicated;
    applying the at least one classifier to the sensor data to predict a user state of the first user based on, the determined at least one effect or side-effect at the period when the first user is scheduled to be medicated with the medication and based on the determined business venue, wherein predicting the user state comprises predicting wandering by determining a gait of walking based on the accelerometer acceleration data, a threshold for predicting the user state corresponding to the determined business venue;
    transmitting a request to the first user to confirm the predicted user state; and
    transmitting a notification regarding the predicted user state to a second user responsive to a confirmation by the first user of the predicted user state or a failure of the first user to respond to the request.

2. The computer-implemented method of claim 1, wherein the predicted user state is a medical anomaly.

3. The computer-implemented method of claim 1, the at least one classifier comprising a first classifier and a second classifier for predicting the user state, wherein:
   the predetermined condition data further comprises an indication of when the first user is scheduled to be performing a particular physical activity;
   the first classifier for predicting the user state corresponds to a period when the first user is not scheduled to be performing the particular physical activity;
   the second classifier for predicting the user state corresponds to a period when the first user is scheduled to be performing the particular physical activity; and
   the user state of the first user is predicted based on the first classifier during the period when the first user is not scheduled to be performing the particular physical activity, and the user state of the first user is predicted based on the second classifier during the period when the first user is scheduled to be performing the particular physical activity.

4. The computer-implemented method of claim 3, wherein the sensor data further comprises GPS data comprising location and velocity.

5. The computer-implemented method of claim 1, wherein the user state is at least one of, a fall state, an unconscious state, a wandering state, and a seizure state.

6. The computer-implemented method of claim 1, wherein:
   a first threshold for predicting the user state based on the sensor data corresponds to a period when the first user is not scheduled to be medicated;
   a second threshold for predicting the user state based on the sensor data corresponds to the period when the first user is scheduled to be medicated; and
   the user state of the first user is predicted based on the first threshold during the period when the first user is not scheduled to be medicated, and the user state of the first user is predicted based on the second threshold during the period when the first user is scheduled to be medicated.

7. The computer: implemented method of claim 6, wherein the second threshold for predicting the user state is lower than the first threshold, wherein it is more likely to determine the user state when the first user is scheduled to be medicated.

8. The computer-implemented method of claim 6, wherein the user state is at least one of a fall state, an unconscious state, a wandering state, and a seizure state.

9. The computer-implemented method of claim 1, the at least one classifier comprising a first classifier and a second classifier for predicting the user state based on the sensor data wherein:
   the first classifier for predicting the user state based on the sensor data corresponds to a period when the first user is not scheduled to be medicated;
   the second classifier for predicting the user state based on the sensor data corresponds to the period when the first user is scheduled to be medicated; and
   the user state of the first user is predicted based on the first classifier during the period when the first user is not scheduled to be medicated, and the user state of the first user is predicted based on the second classifier during the period when the first user is scheduled to be medicated.

10. The computer-implemented method of claim 9, wherein the second classifier for predicting the user state is trained wherein it is more likely to determine the user state when the first user is scheduled to be medicated.

11. The computer-implemented method of claim 1, wherein the predetermined condition data further comprises an indication of at least one of a disability or a medical condition associated with the first user.

12. The computer-implemented method of claim 1, wherein a notification is provided to the first user regarding when the first user is scheduled to be medicated with the medication.

13. The computer-implemented method of claim 1, wherein:
   the predetermined condition data further comprises an indication of when the first user is scheduled to be performing a particular physical activity;
   a first threshold for predicting the user state corresponds to a period when the first user is not scheduled to be performing the particular physical activity;
   a second threshold for predicting the user state corresponds to a period when the first user is scheduled to be performing the particular physical activity; and
   the user state of the first user is predicted based on the first threshold during the period when the first user is not scheduled to be performing the particular physical activity, and the user state of the first user is predicted based on the second threshold during the period when the first user is scheduled to be performing the particular physical activity.

14. The computer-implemented method of claim 1, wherein the at least one classifier comprises a plurality of components respectively corresponding to a plurality of user states, wherein each component is configured to resolve a particular collection of inputs to predict a respective one of the plurality of user states.

15. The computer-implemented method of claim 1, further comprising:
   receiving from the first user a confirmation that the prediction of the user state is valid or an indication that the prediction of the user state is invalid; and
   applying the sensor data to the at least one classifier with the indication that the prediction of the user state is valid or invalid to retrain the at least one classifier.

16. The computer-implemented method of claim 1, wherein the sensor data further comprises device position data, and wherein the user state comprises an indication that the first user has fallen.

17. The computer-implemented method of claim 16, wherein the sensor data further comprises device velocity data.

18. The computer-implemented method of claim 1, wherein the sensor data further comprises an indication of distance traveled, and wherein the user state comprises an indication that the first user is unconscious.

19. The computer-implemented method of claim 18, wherein the sensor data further comprises an indication of a lack of velocity as indicated by a global positioning system ("GPS").

20. The computer-implemented method of claim 18, further comprising resolving by the at least one classifier the indication of when the first user is scheduled to be medicated to predict the user state comprising the indication that the first user is unconscious.

21. The computer-implemented method of claim 1, wherein the user state comprises an indication that the first user is having a seizure, the method further comprising:

receiving an indication of at least one of a disability and a medical condition associated with the first user; and
predicting the seizure based on the acceleration data and the indication of the at least one of the disability and the medical condition.

22. The computer-implemented method of claim 1, wherein the sensed data comprises device acceleration data, and the known state comprises at least one of a fall state, an unconscious state, a wandering state, and a seizure state.

23. The computer-implemented method of claim 1, wherein the at least one classifier comprises a decision tree.

24. The computer-implemented method of claim 1, wherein the at least one classifier comprises a decision tree conditioned by a Markov model.

25. The computer-implemented method of claim 1, wherein the at least one classifier comprises a support vector machine.

26. The computer-implemented method of claim 1, further comprising receiving an indication of a predetermined time period, wherein at least one of predicting the user state, transmitting the request or transmitting the notification is performed during the predetermined time period.

27. The computer: implemented method of claim 1, wherein transmitting the request to the first user to confirm the predicted user state comprises initiating a telephone call to the mobile device corresponding to the first user.

28. The computer-implemented method of claim 1, wherein transmitting the request to the first user to confirm the predicted user state comprises initiating a test questionnaire.

29. A computer-implemented method comprising:
receiving training data comprising sensed data and an indication of at least one known state corresponding to the sensed data;
training a classifier using the training data;
receiving sensor data comprising accelerometer acceleration data from a mobile device corresponding to a first user;
determining a business venue corresponding to a geographic area based on mapping data comprising business directory information;
determining the mobile device has entered or exited the geographic area;
applying the classifier to the sensor data comprising the accelerometer acceleration data to predict a user state based at least on the determined business venue and a threshold for predicting the user state corresponding to the determined business venue;
transmitting a request to the first user to confirm the predicted user state; and
transmitting a notification regarding the predicted user state to a second user responsive to a confirmation by the first user of the predicted user state or a failure of the first user to respond to the request.

30. The computer-implemented method of claim 29, wherein the sensor data further comprises GPS position data and GPS velocity data, wherein the method comprises determining the user state based on the determined business venue, acceleration data, the GPS position data, and the GPS velocity data.

31. The computer-implemented method of claim 29, wherein the sensor data further comprises position data, and wherein the user state comprises an indication that the first user is wandering, the method further comprising predicting wandering based on the determined business venue, the acceleration data and the position data.

32. The method of claim 31, wherein the predicting of wandering comprises determining an undirected gait of walking based on the accelerometer acceleration data.

33. The method of claim 31, wherein the predicting of wandering comprises determining a staggering gait of walking based on the accelerometer acceleration data.

34. The method of claim 31, wherein the predicting of wandering comprises determining a frequency of stops and starts based on the accelerometer acceleration data.

35. The computer-implemented method of claim 29, further comprising applying a plurality of classifiers to the sensor data to predict the user state, wherein each of the plurality of classifiers corresponds to at least one unique user state.

36. The computer: implemented method of claim 29, wherein the business venue comprises a designation that the first user is predicted to be active or passive in the business venue, wherein the threshold for predicting the user state is relatively higher if the geographic area corresponds to an active designation, and the threshold for predicting the user state is relatively lower if the geographic area corresponds to a passive designation.

37. The computer-implemented method of claim 36, wherein the classifier incorporates as an input that the business venue corresponds to the active designation.

38. The computer-implemented method of claim 29, wherein the geographic area corresponding to the determined business venue corresponds to a higher threshold for predicting the user state than a geographic area not corresponding to the business venue.

39. The computer-implemented method of claim 29, wherein the classifier incorporates as an input an indication that the mobile device has entered the geographic area.

40. The computer-implemented method of claim 29, further comprising:
receiving an indication of the geographic area;
receiving an indication of a predetermined time period; and
determining the mobile device has entered or exited the geographic area;
wherein at least one of predicting the user state or transmitting the notification is performed responsive to determining the mobile device has entered or exited the geographic area during the predetermined time period.

41. A mobile device corresponding to a first user, the mobile device including at least one memory comprising instructions operable to enable the mobile device to perform a procedure comprising:
receiving training data comprising sensed data and an indication of at least one known state corresponding to the sensed data;
training a classifier using the training data;
generating by an accelerometer of the mobile device acceleration data corresponding to the first user;
performing GPS measurements by the mobile device;
determining a business venue corresponding to a particular geographic area based on mapping data comprising business directory information;
determining based on the GPS measurements by the mobile device that the mobile device has entered the particular geographic area;
applying the classifier to the accelerometer acceleration data to predict a user state based at least on the determined business venue, a threshold for predicting the user state corresponding to the determined business venue;

enabling by the mobile device a request to confirm the predicted user state; and responsive to a failure of the first user to confirm the predicted user state via the mobile device, transmitting a signal for notifying a second user of the predicted user state.

42. A method comprising:

receiving training data comprising sensed data and an indication of at least one known state corresponding to the sensed data;

training a classifier using the training data;

generating by an accelerometer of a mobile device acceleration data corresponding to a first user;

performing GPS measurements by the mobile device;

determining based on the GPS measurements by the mobile device that the mobile device has entered a particular geographic area;

determining a business venue corresponding to the particular geographic area based on mapping data comprising business directory information;

applying the classifier to the accelerometer acceleration data to predict a user state based at least on the determined business venue and a threshold for predicting the user state corresponding to the determined business venue;

enabling by the mobile device confirmation of the predicted user state; and transmitting a notification regarding the predicted user state to a second user responsive to a confirmation by the first user via the mobile device of the predicted user state.

* * * * *